United States Patent [19]

Brown, Jr. et al.

[11] 3,998,860
[45] Dec. 21, 1976

[54] SOLIDIFICATION RETARDATION OF LIQUID CRYSTALLINE COMPOSITIONS WITH STEROID DERIVATIVES OF ISOSTEARYL CARBONATE

[75] Inventors: George T. Brown, Jr., Dayton; Donald B. Clark, Kettering; Donald E. Koopman, Miami Township, all of Ohio

[73] Assignee: Djinnii Industries, Inc., Dayton, Ohio

[22] Filed: July 31, 1975

[21] Appl. No.: 600,842

Related U.S. Application Data

[62] Division of Ser. No. 500,671, Aug. 26, 1974, Pat. No. 3,920,574.

[52] U.S. Cl. .......................................... 260/397.2
[51] Int. Cl.² ......................................... C07J 9/00
[58] Field of Search ................ 260/397.2; 424/238, 424/240

[56] References Cited

UNITED STATES PATENTS

| | | | |
|---|---|---|---|
| 3,657,538 | 4/1972 | Fergason et al. | 260/397.2 |
| 3,776,927 | 12/1973 | Fergason et al. | 260/397.2 |
| 3,888,892 | 6/1975 | Leder | 260/397.2 |

*Primary Examiner*—Elbert L. Roberts
*Attorney, Agent, or Firm*—Ralph L. Marzocco

[57] ABSTRACT

Solidification of liquid crystalline compositions is retarded by incorporating therein compounds which are steroid derivatives of isostearyl carbonate. These novel carbonates which are quite stable to environmental factors such as ultraviolet light exposure, temperature changes, oxidation, etc., retard solidification of liquid crystalline compositions for extended periods of time. Moreover, these compounds, some of which of themselves exhibit color play, can be used in increasing amounts to increasingly narrow the color play range without noticeably decreasing the specular intensity of the color changes of liquid crystalline compositions.

12 Claims, No Drawings

SOLIDIFICATION RETARDATION OF LIQUID CRYSTALLINE COMPOSITIONS WITH STEROID DERIVATIVES OF ISOSTEARYL CARBONATE

This is a division of application Ser. No. 500,671, filed Aug. 26, 1974, now U.S. Pat. No. 3,920,574.

BACKGROUND OF THE INVENTION

1. Field of the Invention

This invention relates to a novel group of chemical compounds which are steroid derivatives of isostearyl carbonate, to the use thereof as solidification retarders in liquid crystalline compositions, to the solidification retarded compositions, to the manufactured articles made therefrom.

2. Description of the Prior Art

Liquid crystals may be defined as that class of matter which has an intermediate or mesomorphic state in which these substances behave mechanically as liquids yet exhibit many optical properties of crystals. The mesomorphic state or liquid crystalline phase is obtained either by heating liquid crystals that are in the solid phase or by cooling liquid crystals that are in the liquid phase. Liquid crystal substances have been classified as belonging in one of three different types, viz., cholesteric, nematic and smectic. The cholesteric structure is distinguished from the nematic and smectic structures by its markedly different optical properties, for example, cholesteric materials are optically negative whereas nematic and smectic materials are optically positive.

Thin films of cholesteric liquid crystals upon interaction with light exhibit a property, termed selective scattering, whereby light rays impinging upon the film may leave at an angle unrelated to the angle of incident light. The color and intensity of the scattered light depends upon the temperature of the scattering material and upon the angle of incident illumination. The range of temperatures within which visible colors are displayed as a result of scattering of white light from cholesteric liquid crystals is known as the color play range. A color play range may be made as wide as 30° C. or more (for example, start of red at 37° C. through the visible color spectrum with start of blue at 67° C.) or may be as narrow as 1° C. (for example, start of red at 30° C. through the visible color spectrum with start of blue at 31° C.).

Many liquid crystalline materials having once been melted, tend to solidify in a short period of time. U.S. Pat. No. 3,580,864 describes the use of a compound, cholesteryl erucyl carbonate, to stabilize cholesteric-phase liquid-crystal compositions against true-solid formation. However, perhaps because of the erucyl carbon-carbon double bond, this compound is not as able to resist ultraviolet light degradation as are the novel compounds of this invention.

The production of steroid alkyl carbonates is well known to persons skilled in the art of steroid synthesis. By way of example one method, but not necessarily the preferred, involves the reaction of alkyl chloroformate (either as a reagent or synthesized in situ by the reaction of phosgene with an alkanol) with pyridine and a sterol. Insoluble pyridine hydrochloride which is precipitated is filtered from the reaction mixture. The oily alkyl steroid carbonate layer is separated from the filtrate by means of a separatory funnel and repeatedly washed with methanol.

BRIEF SUMMARY OF THE INVENTION

Many liquid crystalline compositions after a period of time varying from hours to weeks become unstable and solidify as crystals. The addition of certain steroid derivatives of isostearyl carbonate retards this solidification process and thereby extends the mesomorphic life of these compositions. These solidification retardants are effective at low temperatures as well as at elevated and room temperatures.

SYNTHESIS DESCRIPTION OF STEROID DERIVATIVES OF ISOSTEARYL CARBONATE

Steroids are a family of compounds which contain the perhydro-1,2-cyclopentanophenanthrene ring system. A steroid group of $C_{27}$–$C_{29}$ secondary alcohols of animal or plant origin differs from common alcohols in that they are crystalline solids of melting points in the range of 100°–200° C. Cholesterol, a $C_{27}H_{45}OH$ monounsaturated sterol, is found only in the animal world as is cholestanol, a companion compound, which is the product of cholesterol hydrogenation.

Although cholesterol is not found in the plant world, a number of closely related sterols, known as phytosterols, are encountered. For example, stigmasterol, $C_{29}H_{47}OH$, is a phytosterol found as a component of a sterol mixture from soybean oil. The nonsaponifiable fraction from soybean oil contains 12–25% of stigmasterol and the remainder is a mixture of sitosterols, $C_{29}H_{49}OH$, which are largely monounsaturated carbon 5 - carbon 6 stenols.

Cholesterol, stigmasterol and sitosterol are typical members of a group of sterols comprising a cyclopentenophenanthrene system. The structure and numbering of cyclopentenophenanthrene is

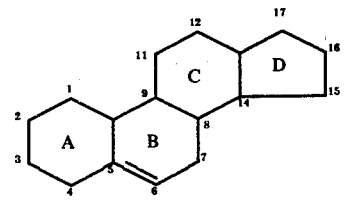

(Fieser, L. F. & Fieser, M. Steroids, N.Y., Rheinhold, 1959, p.l., 346–348.).

The following synthesis of cholesteryl isostearyl carbonate is a description of a typical synthesis of a steroid isostearyl carbonate. The steroid is derived from a group of sterols comprising cholesterol, stigmasterol and sitosterol; the halosterols of cholesterol, stigmasterol and sitosterol; and the group of sterols in which the carbon 5 - carbon 6 unsaturated bond of cholesterol, stigmasterol and sitosterol is saturated.

Cholesteryl isostearyl carbonate can be synthesized either by the chemical reaction of isostearyl alcohol with cholesteryl chloroformate or by the chemical reaction of isostearyl chloroformate with cholesterol. Cholesteryl chloroformate is available as a reagent or can be synthesized by slowly bubbling phosgene gas through a solution of cholesterol dissolved in anhydrous ethyl ether. This is illustrated by the following chemical reaction:

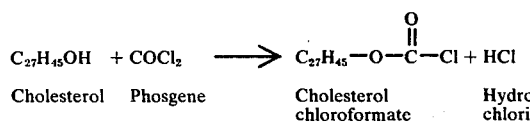

Cholesterol    Phosgene      Cholesterol    Hydrogen
                                  chloroformate    chloride Cholesteryl chloroformate is chemically reacted with isostearyl alcohol and pyridine to yield cholesteryl isostearyl carbonate and pyridine hydrochloride. The pyridine hydrochloride precipitates out of the benzene solution and is separated from the cholesteryl isostearyl carbonate by means of filtration. The cholesteryl isostearyl carbonate is then isolated from the filtrate. This is illustrated by the following chemical reaction:

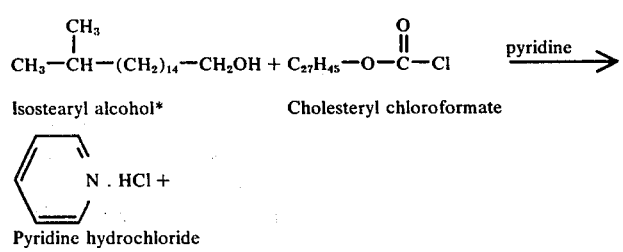

Isostearyl alcohol*      Cholesteryl chloroformate

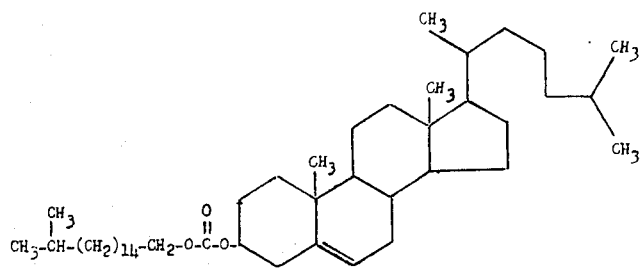

Cholesteryl isostearyl carbonate

*Isostearyl alcohol is sold as ADOL 66 by Ashland Chemical Company, Columbus, Ohio, United States of America.

The laboratory synthesis of cholesteryl isostearyl carbonate was performed in a three-neck pyrex reaction flask with ground glass joints to which was fitted an addition funnel, a reflux condenser, and a stirrer. The flask was heated by means of a voltage controlled heating mantle. Into the flask 336.9 grams (0.75 mol) of cholesteryl chloroformate were added to 500 milliliters of benzene and heated until the cholesteryl chloroformate dissolved into solution. In a separate flask 205.5 grams (0.76 mol) of isostearyl alcohol were dissolved into 300 milliliters of benzene by the application of heat. The isostearyl alcohol solution was then added to the solution of cholesteryl chloroformate.

Through the use of an addition funnel 60.7 milliliters (0.75 mol) of pyridine dissolved in 100 milliliters of benzene were added dropwise to the contents of the flask. An exothermic reaction followed resulting in the formation of a white solid consisting of pyridine hydrochloride. After complete addition of pyridine, the contents of the flask were refluxed for 1.5 hours at a temperature of about 80° C.

The pyridine hydrochloride was removed by vacuum filtration, using a Buchner funnel and then methanol was added with agitation to the filtrate solution of cholesteryl isostearyl carbonate and benzene. An oily product, cholesteryl isostearyl carbonate which was phased out of solution, was separated from the methanol-benzene phase by means of a separatory funnel. The consistency of the resultant cholesteryl isostearyl carbonate changes from an oil to grease as the temperature is lowered, but even after prolonged storage at low temperatures the product did not solidify into a true solid. When used by itself the compound has a color-play range of about 23.5° C. to 24.0° C.

DESCRIPTION OF THE PREFERRED EMBODIMENTS

Steroid derivatives of isostearyl carbonate are used by incorporating them, in amounts up to 100%, in liquid crystalline compositions. Reference may be made to U.S. Pat. No. 3,620,889, lines 16–42, column 5 for a comprehensive (but by no means complete) list of compounds suitable for use in making such compositions. The preferable use of these carbonates is 10 to 80 weight per cent of the liquid crystalline composition; however they are effective when used in amounts as low as 5 weight per cent or less, and they can be used in amounts approaching 100 weight per cent of liquid crystalline compositions.

The following examples are illustrative of the process and products of the present invention and are not to be construed as limiting.

EXAMPLE I

To compositions of equal parts of cholesteryl pelargonate (CP) and cholesteryl oleyl carbonate (COC) was added cholesteryl isostearyl carbonate (CIC) in quantitative increments up to about 40 weight per cent. These compositions were melted together and coated onto a black coated temperature probe to a thickness of about 1 to 4 thousandths of an inch. Color was read perpendicular to the surface with the light also normal to the surface of the liquid crystalline films.

Table I presents examples that illustrate the use of

CIC with CP and COC, typical liquid crystalline materials, and the effect of the event temperature and the color play temperature range.

Table I

| Wt. % CIC | Wt. % CP | Wt. % COC | Temp. (° C.) Start Of | |
|---|---|---|---|---|
| | | | Red | Blue |
| 0.0 | 50.0 | 50.0 | 33.3 | 34.1 |
| 9.2 | 45.4 | 45.4 | 31.7 | 32.5 |
| 17.4 | 41.3 | 41.3 | 30.4 | 31.1 |
| 26.6 | 36.7 | 36.7 | 28.9 | 29.5 |
| 36.0 | 32.0 | 32.0 | 27.4 | 27.8 |

The addition of CIC depressed the onset of the color event temperatures of both the red and blue end of the spectrum, and at the same time, as more CIC was added, especially with additions exceeding ten per cent by weight, the entire spectrum from red to blue or the color play range was narrowed. In all these compositions the intensity of the spectrum as displayed to the eye did not appreciably vary.

EXAMPLE II

To compositions of decreasing amounts of cholesteryl pelargonate (CP) were added increasing amounts from 10.0 to 80.0 weight per cent of cholesteryl isostearyl carbonate (CIC). These compositions were melted together and coated onto a black coated temperature probe to a thickness of about 1 to 4 thousandths of an inch. Color was read perpendicular to the surface with the light also normal to the surface of the liquid crystalline film.

Table II presents examples that illustrate the use of CIC with CP, a typical liquid crystalline material, and the resulting color play temperature range.

Table II

| Wt. % CIC | Wt. % CP | Temp. (° C.) Start Of | |
|---|---|---|---|
| | | Red | Blue |
| 80.0 | 20.0 | 23.0 | 23.4 |
| 65.0 | 35.0 | 28.0 | 28.5 |
| 50.0 | 50.0 | 35.1 | 35.8 |
| 30.0 | 70.0 | 48.2 | 48.9 |
| 20.0 | 80.0 | 56.3 | 56.9 |
| 10.0 | 90.0 | 63.5 | 65.1 |

Compared to a liquid crystalline system consisting of a series of compositions comprising cholesteryl oleyl carbonate (COC) and cholesteryl pelargonate (CP) the above CIC and CP system on a weight per cent basis, is approximately 2° C. higher but is more fluid throughout the entire range without degrading optical properties.

EXAMPLE III

Both an 80/20 by weight per cent composition of cholesteryl pelargonate (CP)/cholesteryl oleyl carbonate (COC) and an 80/20 by weight per cent composition of cholesteryl pelargonate (CP)/cholesteryl isostearyl carbonate (CIC), after heated to an isotropic melt, were subjected to a temperature of 5° C. Samples were periodically tested to determine a composition solidification point. The CP/COC composition solidified in about 3¼ hours, whereas the CP/CIC composition was still fluid indicating solidification retardation due to the isostearyl fraction of the CIC molecule. Other CP/COC to CP/CIC ratios yielded the same result, that is, CIC containing compositions were still fluid whereas COC containing compositions were solid.

EXAMPLE IV

An 80/20 by weight per cent composition of cholesteryl pelargonate (CP)/sitosteryl oleyl carbonate (SOC) and an 80/20 by weight per cent composition of cholesteryl pelargonate (CP)/sitosteryl isostearyl carbonate (SIC), after heated to an isotropic melt, were subjected to a temperature of 5° C. Samples were periodically tested to determine a composition solidification point. The CP/SOC composition solidified in about ¾ hour whereas the CP/SIC composition was still fluid indicating solidification retardation due to the isostearyl of the SIC molecule.

EXAMPLE V

To compositions of decreasing amounts of cholesteryl pelargonate (CP) were added increasing amounts from 10.0 to 50.0 weight per cent of sitosteryl isostearyl carbonate (SIC). These compositions were melted together and coated onto a black coated temperature probe to a thickness of about 1 to 4 thousandths of an inch. Color was read perpendicular to the surface with the light also normal to the surface of the liquid crystalline film.

Table III presents examples that illustrate the use of SIC with CP, a typical liquid crystalline material, and the resulting color play temperature range.

Table III

| Wt. % CP | Wt. % SIC | Temp. (° C.) Start Of | | |
|---|---|---|---|---|
| | | Red | Green | Blue |
| 90.0 | 10.0 | 59.0 | 60.0 | 61.0 |
| 80.0 | 20.0 | 46.0 | 47.5 | 49.0 |
| 70.0 | 30.0 | 41.0 | 41.5 | 43.0 |
| 50.0 | 50.0 | — | Nothing | — |

Unlike cholesteryl isostearyl carbonate (CIC), SIC exhibits no detectable visible color play, however it can be used in combinations with other liquid crystalline materials to retard solidification without degrading optical properties of the various compositions.

EXAMPLE VI

To compositions of decreasing amounts of cholesteryl pelargonate (CP) were added increasing amounts from 10.0 to 50.0 weight per cent of stigmasteryl isostearyl carbonate (StIC). These compositions were melted together and coated onto a black coated temperature probe to a thickness of about 4 thousandths of an inch. Color was read perpendicular to the surface with the light also normal to the surface of the liquid crystalline film.

Table IV presents examples that illustrate the use of StIC with CP, a typical liquid crystalline material, and the resulting color play temperature range.

Table IV

| Wt. % CP | Wt. % StIC | Temp. (° C.) Start Of | | |
|---|---|---|---|---|
| | | Red | Green | Blue |
| 90.0 | 10.0 | 63.0 | 64.0 | 65.0 |
| 80.0 | 20.0 | 55.5 | 56.5 | 57.5 |
| 70.0 | 30.0 | 50.0 | 51.5 | 53.0 |
| 50.0 | 50.0 | (Faint blue blush 40–45° C.) | | |

Unlike cholesteryl isostearyl carbonate (CIC), StIC exhibits no detectable visible color play, however it can be used in combination with other liquid crystalline materials to retard solidification without degrading optical properties of the various compositions.

The data of EXAMPLES V and VI indicate that animal and plant derived steroid materials can be combined to yield useful liquid crystalline compositions.

EXAMPLE VII

To 48.5 parts of cholesteryl isostearyl carbonate (CIC), 44.9 parts cholesteryl pelargonate (CP), and 1.8 parts cholesteryl chloride (CCl) was added 4.8 parts p-(p'-ethoxy phenyl azo) phenyl hexanoate. All components were added by weight per cent. The spectrum produced by this composition displayed an enhanced brillance which was attributed to the addition of the nematic liquid crystalline material, p-(p'-ethoxy phenyl azo) phenyl hexanoate. This nematic reduced the viscosity of the composition and synergistically with CIC prevented solidification for much longer periods of time, and at lower storage temperatures than has heretofore been possible, and further stabilized liquid crystalline compositions when they were exposed to aging, temperature, oxygen, ultraviolet, or sunlight tests.

EXAMPLE VIII

To 40.0 parts of cholesteryl pelargonate (CP) and 40.0 parts cholesteryl isostearyl carbonate (CIC) was added 20.0 parts cholesteryl 2-ethyl hexyl carbonate (CEHC). All components were added by weight per cent. These materials were heated to produce an isotropic melt which was coated onto a black coated temperature probe to a thickness of about 1 to 4 thousandths of an inch. Color was read perpendicular to the surface with the light also normal to the surface of the film. The composition exhibited a brillant color display with start of red at about 10° C. and start of blue at about 17° C. CEHC has no visible color play range when subjected to temperatures of −10° C. to +100° C. The material became a clear glass between −5° C. and −10° C. CEHC reduced the viscosity of the composition and synergistically in combination with CIC prevented solidification for even longer periods of time, and at lower storage temperatures than has heretofore been possible with similar compositions containing no CIC.

EXAMPLE IX

A composition of equal parts by weight of cholesteryl pelargonate (CP) and cholesteryl isostearyl carbonate (CIC) was microencapsulated according to the teachings disclosed in U.S. Pat. No. 2,800,457, issued July 23, 1957, on the application of Barrett K. Green and Lowell Schleicher. The resultant microencapsulated liquid crystalline composition was mixed on an equal weight basis with a 10 per cent by weight aqueous solution of polyvinyl alcohol (PVA). The PVA used is about 87 to 89 per cent hydrolyzed, and is characterized by exhibiting a viscosity of about 35 to 45 centipoises in a 4 per cent by weight, aqueous solution at 20° C. (such as material designated by the trademark, "Elvanol 50-42" sold by E. I. duPont de Nemours and Co., Wilmington, Del., U.S.A.). The resulting slurry was coated onto (a) black construction paper, and (b) polyester film.

The coated black paper, when subjected to a gradually increasing temperature, exhibited a brilliant color display with start of red at about 35° C. and start of blue at about 36° C.

The PVA/liquid crystalline composition coating was stripped from the polyester film and coated with a black paint. The resultant matrix exhibited a color play range substantially identical to the coating on black construction paper.

EXAMPLE X

Twenty grams of a 65/35 by weight composition of cholesteryl isostearyl carbonate (CIC)/cholesteryl pelargonate (CP), heated until it was an isotropic melt, was emulsified into 100 grams of a 10 per cent by weight aqueous solution of polyvinyl alcohol (PVA, such as "Elvanol 50-42"). The emulsion was coated at ambient temperature onto a black glass substrate. The resultant liquid crystalline composition embedded in a PVA matrix exhibited a color play range with start of red at about 28.0° C. and start of blue at about 28.5° C.

In view of the teachings and examples, it is apparent that the effects and advantages of the invention, especially retardation of solidification of liquid crystalline compositions for an extended period of time, can be obtained by preparing and incorporating effective amounts of compounds which are steroid derivatives of isostearyl carbonate.

Although the foregoing teachings and examples relate to cholesteryl isostearyl carbonate, sitosteryl isostearyl carbonate and stigmasteryl isostearyl carbonate, it will be possible to prepare and obtain results substantially similar with other compounds closely related in structure and properties. For example, it is apparent that the carbon 5 - carbon 6 position of the cyclopentenophenanthrene ring system may be saturated with hydrogen and/or halogen to yield cholestanol, halocholestanol, sitostanol, halositostanol, stigmastanol or halostigmastanol, and the corresponding isostearyl carbonates made from these compounds may be expected to exhibit similar solidification retardation effects.

Thus it is apparent that the invention affords a new class of cholesteric-phase and nematic-phase liquid crystalline solidification retarded compositions that will find use in such applications as thermal-pattern sensing devices, vapor-detecting devices, rate of shear sensing devices, electronic sensing devices, magnetic sensing devices and the like.

While we have shown and described herein certain embodiments of our invention, we intend to cover as well any change or modification therein which may be made without departing from its spirit and scope.

We claim as our invention:

1. A composition of matter for use in retarding solidification of liquid crystalline compositions comprising of about 20–90 weight per cent cholesteryl pelargonate, about 0–50 weight per cent cholesteryl oleyl carbonate, about 0–1.8 weight per cent cholesteryl chloride and a compound having the formula

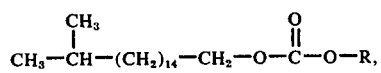

wherein R is a derivative of a steroid group selected from the group consisting of cholesterol, stigmasterol and sitosterol; and where the chemical bond linkage of carbon 5 to 6

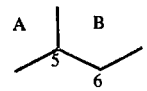

of said steroid group is selected from a group consisting of

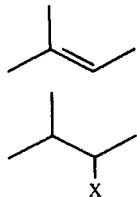 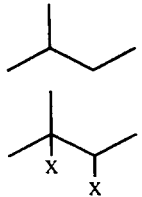

X being a halogen.

2. The composition as defined in claim 1, characterized in that said compound is cholesteryl isostearyl carbonate.

3. The composition as defined in claim 1, characterized in that said compound is stigmasteryl isostearyl carbonate.

4. The composition as defined in claim 1, characterized in that said compound is sitosteryl isostearyl carbonate.

5. The composition as defined in claim 1, characterized in that said compound is cholestanyl isostearyl carbonate.

6. The composition as defined in claim 1, characterized in that said compound is halocholestanyl isostearyl carbonate.

7. The composition as defined in claim 1, characterized in that said compound is stigmastanyl isostearyl carbonate.

8. The composition as defined in claim 1, characterized in that said compound is sitostanyl isostearyl carbonate.

9. The composition as defined in claim 1, characterized in that said compound is halostigmastanyl isostearyl carbonate.

10. The composition as defined in claim 1, characterized in that said compound is halositostanyl isostearyl carbonate.

11. The composition as defined in claim 2, characterized in that said composition contains about 4.8 weight per cent p-(p'-ethoxy phenyl azo) phenyl hexanoate.

12. The composition as defined in claim 2, characterized in that said composition contains about 20.0 weight per cent cholesteryl 2-ethyl hexyl carbonate.

* * * * *